US00PP20953P2

(12) United States Plant Patent
Tomerlin

(10) Patent No.: US PP20,953 P2
(45) Date of Patent: Apr. 27, 2010

(54) CLIMBING ROSE PLANT NAMED 'MARGARET MAE'

(50) Latin Name: ***Rosa hybrida*/Climbing Shrub Rose Plant**
Varietal Denomination: Margaret Mae

(76) Inventor: Reggie Joe Tomerlin, 1353 Brampton Rd., Los Angeles, CA (US) 90041

( * ) Notice: Subject to any disclaimer, the term of this patent is extended or adjusted under 35 U.S.C. 154(b) by 0 days.

(21) Appl. No.: 12/584,855

(22) Filed: Sep. 14, 2009

(51) Int. Cl.
*A01H 5/00* (2006.01)

(52) U.S. Cl. ..... Plt./114

(58) Field of Classification Search ..... Plt./114, Plt./109
See application file for complete search history.

(56) References Cited

U.S. PATENT DOCUMENTS

PP6,892 P 7/1989 Meilland
PP18,952 P2 6/2008 Kordes
PP19,263 P2 9/2008 Meilland
PP19,433 P2 11/2008 Redler
PP19,952 P2 4/2009 Lim

*Primary Examiner*—Annette H Para
(74) *Attorney, Agent, or Firm*—Justin Leisey

(57) ABSTRACT

A new and distinct variety of climbing shrub rose plant is provided which forms in abundance on a substantially continuous basis attractive clusters of fully double, deep pink blossoms having approximately 70–80 petals on average. The new variety is a spontaneous mutation of unknown causation of the 'Meiviolin' variety (U.S. Plant Pat. No. 6,892). The deep pink color can be readily distinguished from the white-pink color of the 'Meiviolin' variety. Vigorous vegetation is formed. The foliage is dense medium green with a semi-glossy finish. Excellent resistance to Black Spot and powdery mildew is displayed. Attractive dense ornamentation in the form of foliage and blossoms is made possible when the new variety is grown on a support.

2 Drawing Sheets

Figures 1, 2, 3, 4, 5, 6, 7, 8, 9, 10, 11, 12:
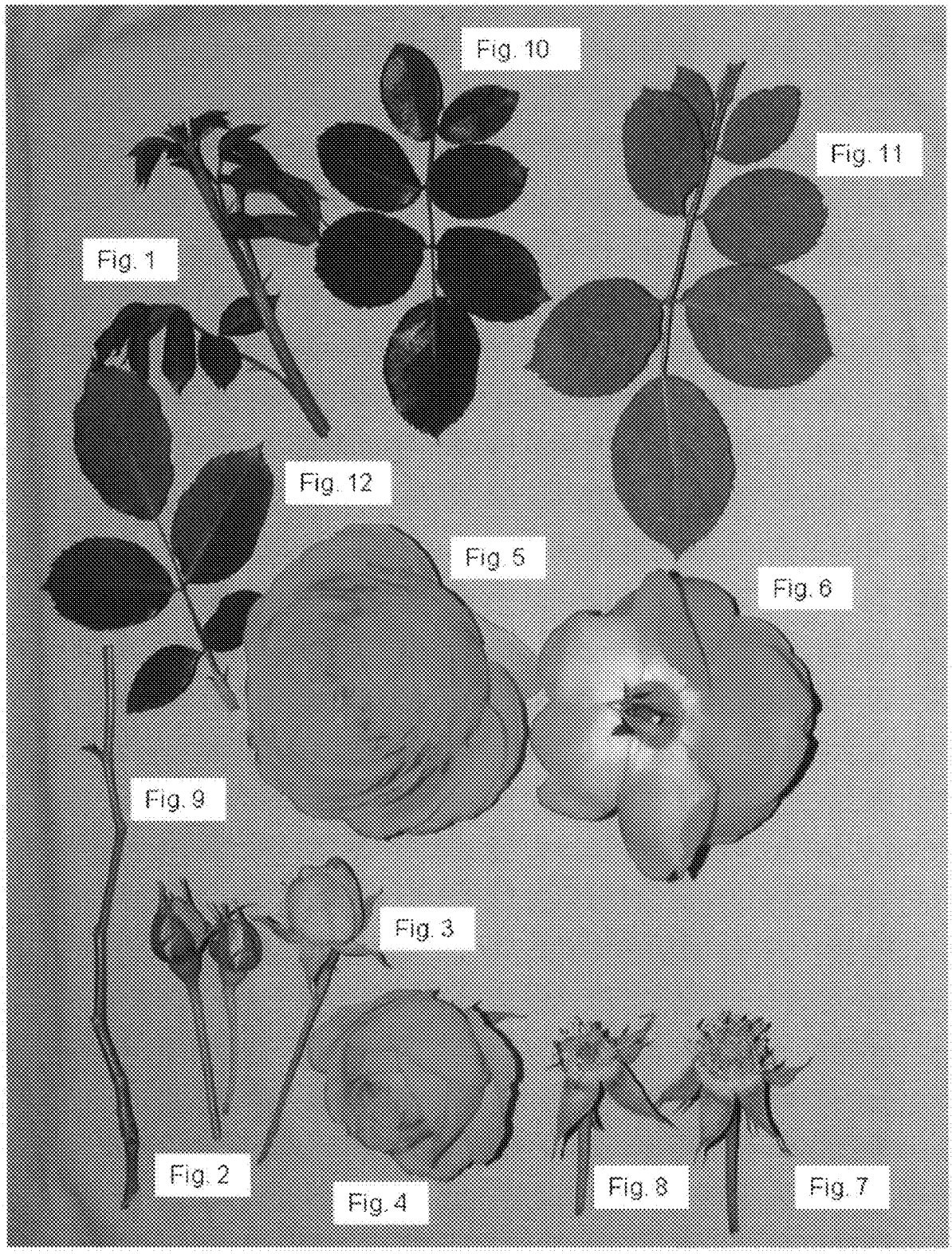

Botanical/commercial classification: *Rosa hybrida*/Climbing Shrub Rose Plant.

Varietal denomination: cv. 'Margaret Mae'.

SUMMARY OF THE INVENTION

The new variety of *Rosa hybrida* climbing shrub rose plant of the present invention was discovered during April, 2002 growing on a single specimen of the rose plant of the 'Meiviolin' variety (U.S. Plant Pat. No. PP6,892). It was growing in my cultivated rose garden at Riverside, Calif., USA. The rose is distinctive because of its color, which is markedly different from the parental variety. It was borne on one of five branches, with the roses of the other branches appearing to be true to variety. I proceeded to preserve the new variety by carefully removing the other branches, allowing the new rose the full benefit of the root system. The new variety is believed to be a spontaneous naturally-occurring mutation of the 'Meiviolin' variety of unknown causation.

It was found that the new variety of climbing shrub rose plant of the present invention possesses the following combination of characteristics:

(a) abundantly and continuously forms attractive and long lasting very double deep pink blossoms which exhibit a globular rose shape, (b) exhibits vigorous vegetation (in Los Angeles, Calif., USA it retains the majority of its foliage throughout the winter months), (c) exhibits excellent resistance to frost, and (d) is particularly well suited for growing in the landscape because of its vigor, beauty, and ability to scale walls, fences, and trellises when given such means of support (absolutely no dead or dying canes having been observed).

(e) exhibits excellent resistance to Black Spot and powdery mildew.

The new variety meets the needs of the horticultural industry. It can be grown to advantage as an attractive ornamentation in parks, gardens, public areas, and residential landscapes. I believe that it will enjoy wide acceptance and usage, owing to its striking color and vigor. It also grows particularly well in containers developing a fine, dense root system on its own roots.

The new variety of *Rosa hybrida* climbing shrub rose plant of the present invention can be readily distinguished from the 'Meiviolin' variety (U.S. Plant Pat. No. PP6,892) by the marked difference in its color. Unlike the new variety, 'Meiviolin' is "creamy white in color edged with carmine pink". On the contrary, the color of the present invention is a deep pink in sharp contrast to the parental variety. The color of the buds is noticeably darker as described below. Notice of this distinction was my first observation that a mutation had occurred. Although the parent variety is vigorous, the new variety is so vigorous as to have no need of grafting on other rootstocks. This will serve it well in geographical areas where particularly harsh or untimely freezes occur. New shoots coming from the ground are true to type and have successively larger size (caliper and length) than prior ones allowing the plant to expand its reach quickly, proving its classification as a "climber". The scent, although similar to the parent, possesses a noticeably stronger, sweet, floral vintage rose scent. The number of petals varies with flower size, but averages from 70 to 80, while the flower of the parent averages from 55 to 60.

The characteristics of the new variety have been found to be homogeneous and stable and are transmissible by asexual propagation from one generation to another. The plant has been successfully asexually propagated in Los Angeles, Calif., USA by rooted stem cuttings and have been reproduced true to type in successive generations. The characteristics of the new variety are transmitted true to type from one generation to another by such asexual propagation. The plant propagates well and grows very well on its own roots.

The new variety has been named the Margaret Mae variety.

BRIEF DESCRIPTION OF THE PHOTOGRAPHS

The accompanying photographs show, as nearly true as it is reasonably possible to make the same in color illustrations of this character, typical specimens of the plant parts of the new variety, as well as a specimen of a typical plant of the new variety while growing in the landscape. The rose plants of the new variety illustrated herein were two years of age and were grown in a cultivated residential garden at Los Angeles, Calif., USA. on their own roots. Photographs were prepared on Apr. 30, 2007.

Figure 13:
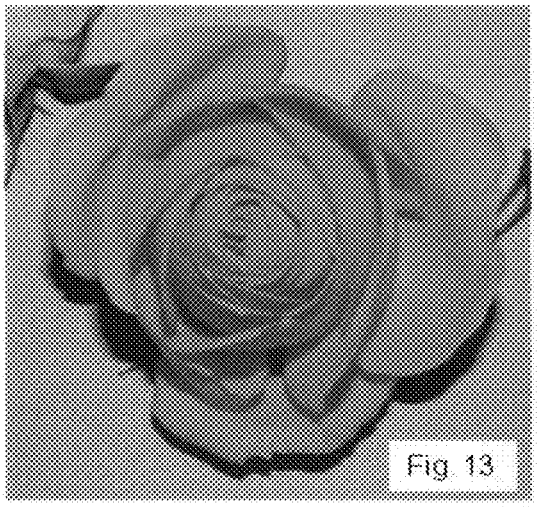
Figure 15:
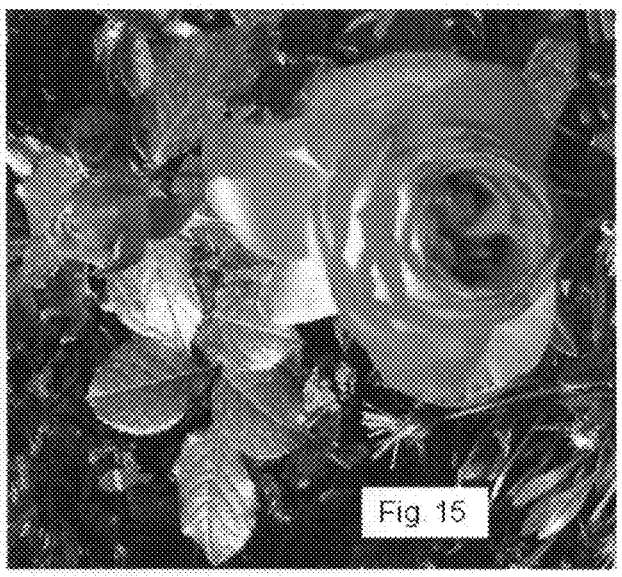
Figure 14:
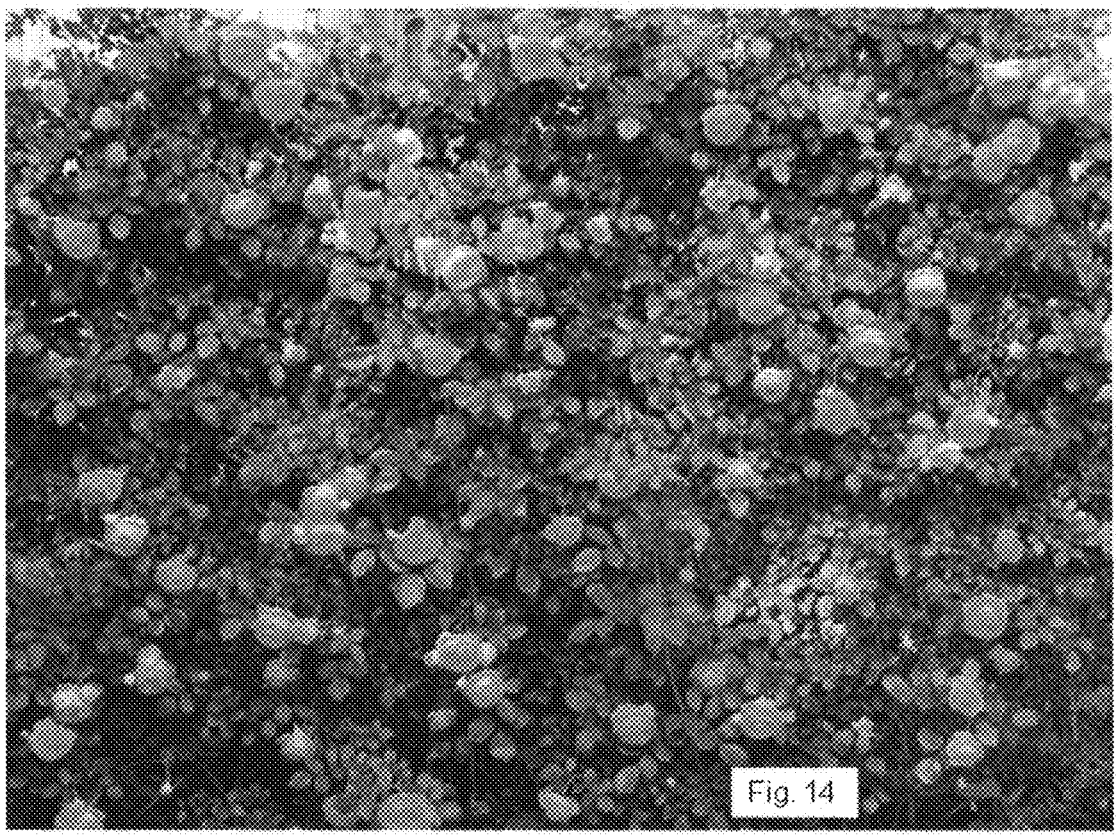

FIG. 1—illustrates a specimen of a young shoot with leaves;

FIG. 2—illustrates a specimen of a floral buds before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of an open flower—plan view—obverse;

FIG. 6—illustrates a specimen of an open flower—plan view—reverse;

FIG. 7—illustrates a specimen of a floral receptacle showing the arrangement of the stamens and pistils;

FIG. 8—illustrates a specimen of a floral receptacle showing the arrangement of the pistils (stamens removed);

FIG. 9—illustrates a specimen of a main branch;

FIG. 10—illustrates specimens of mature leaves with 7 leaflets—plan view—upper surface;

FIG. 11—illustrates specimens of mature leaves with 7 leaflets—plan view—lower surface;

FIG. 12—illustrates specimens of immature leaves with 5 leaflets—plan view—upper surface;

FIG. 13—illustrates a floral bud at the opening of the petals and illustrating the globular shape and large petal count of the flower;

FIG. 14—illustrates specimens of a typical multiple flowering plants while being grown in the landscape with the support of an iron trellis;

FIG. 15—illustrates a fully open flower, floral bud and leaves of the original spontaneous mutation grown at Riverside, Calif., USA. The mutation was a single branch of five total branches on the parental plant.

DETAILED DESCRIPTION

The chart used in the identification of colors is that of The Royal Horticultural Society (R.H.S. Colour Chart). The description is based on two year old specimens of the new variety during May while grown in the open air in Los Angeles, Calif., USA.

Class: Climbing Shrub.

Plant:

*Height.*—Approximately 70 to 80 inches when growing on their own roots in Los Angeles, Calif., USA.

*Habit.*—Climbing.

Branches:

*Color.*—Young stems: light green, Yellow-Green Group 146D. Adult wood: light green, Yellow-Green Group 146C.

*Thorns.*—Present. Incidence: 8 per 4 inches of stem. Average length: ¼ inch. Color: Immature thorns: Moderate Yellowish Green Group RHS 146C, Mature thorns: Light Olive Brown Group RHS 199B. Shape: Concave to slightly downward hooked.

*Texture.*—The stems are smooth and lustrous in texture.

Leaves:

*Stipules.*—Adnate, pectinate, wide and linear.

*Petioles.*—Upper surface: grooved, reddish-brown on young foliage, medium green on mature foliage with more or less glandular edges. Under surface: light green with some small hooked thorns.

*Leaflets.*—Number: 3, 5, and 7 (most often). Shape: oval. Serration: simple and regular. Texture: firm. Overall appearance: dense foliage with a glossy to semi-glossy aspect. Color (young foliage): upper surface: Strong Greenish Yellow, RHS 151C; Suffused with a deep red tint. Under surface: Brilliant Yellowish Green, RHS 154C. Color (adult foliage): upper surface: Strong Yellowish Green, RHS 145A. Under surface: Light Yellowish Green, RHS 142 C.

Inflorescence:

*Number of flowers.*—Generally one blossom per stem.

*Peduncle.*—Smooth, green, straight, rigid, approximately 2.75 inches in length on average.

*Sepals.*—Greenish in coloration. Under surface: medium green in coloration with a reddish tint, often with glandular appendiculated edges.

*Buds.*—Shape: very double, globe shaped. Length: approximately 1 in. on average. Color: upper surface: Deep Pink, RHS 52B. Under surface: substantially the same as the upper surface.

*Flower.*—Form: very double, globe shaped and opening fully double, flattened oblate spheroid. Diameter: approximately 3 to 4 inches on average. Color: upper surface: Deep Pink, RHS 52C, edged with a thin border of Deep Pink, RHS 52B. Under surface: substantially the same as the upper surface. Fragrance: moderate, sweet, floral vintage rose scent. Flower duration: long. Petal form: flattened with more or less reflected edges. Petal texture: firm. Petal number: approximately 70 to 80. Petal drop: good. Stamen number: approximately 160 to 165 on average. Anthers: normal, straw yellow in coloration and edged with dark ochre. Filaments: normal, yellowish. Pistils: approximately 145 to 150 on average. Stigmas: normal, straw colored, located beyond the anthers. Styles: free, straw colored with a bright violet top, of very irregular heights.

Development:

*Vegetation.*—Vigorous.

*Blossoming.*—Abundant and continuous.

*Aptitude to bear fruits.*—None.

*Resistance to frost.*—Very good.

*Resistance to diseases.*—Excellent.

Plants of the 'Margaret Mae' variety have not been observed under all possible environmental conditions to date. Accordingly, it is possible that the phenotype may vary somewhat with variations in the environment, such as temperature, light, etc.

I claim:

1. A new and distinct variety of climbing shrub rose plant characterized by the following combination of characteristics:

(a) abundantly forms on a substantially continuous basis attractive clusters of fully double blossoms that are deep pink in coloration, (b) exhibits an upright climbing growth habit, (c) forms vigorous vegetation, (d) forms dense medium green foliage having a semi-glossy finish, and (e) exhibits excellent resistance to Black Spot and powdery mildew;

substantially as herein shown and described.

* * * * *